(12) United States Patent
Gebhardt

(10) Patent No.: US 8,193,506 B2
(45) Date of Patent: Jun. 5, 2012

(54) DEVICE FOR DETECTING SIGNALS

(75) Inventor: Matthias Gebhardt, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 527 days.

(21) Appl. No.: 12/385,988

(22) Filed: Apr. 27, 2009

(65) Prior Publication Data

US 2009/0271153 A1    Oct. 29, 2009

(30) Foreign Application Priority Data

Apr. 28, 2008    (DE) .......................... 10 2008 021 170

(51) Int. Cl.
*G01T 1/161* (2006.01)
(52) U.S. Cl. .................................. 250/363.04
(58) Field of Classification Search ............. 250/363.02, 250/363.03, 363.04, 363.08, 363.09, 370.11; 702/189
See application file for complete search history.

(56) References Cited

U.S. PATENT DOCUMENTS

| | | | | |
|---|---|---|---|---|
| 4,609,825 A * | 9/1986 | Berger et al. | ................ | 348/324 |
| 4,672,207 A * | 6/1987 | Derenzo | ................ | 250/363.02 |
| 4,945,242 A * | 7/1990 | Berger et al. | ................ | 250/367 |
| 2006/0065845 A1* | 3/2006 | Yamaguchi | ............ | 250/370.09 |

FOREIGN PATENT DOCUMENTS

| | | |
|---|---|---|
| DE | 68905851 T3 | 9/1989 |
| DE | 69728894 T2 | 8/1999 |
| DE | 69835240 T2 | 7/2001 |
| DE | 102004055939 B4 | 5/2007 |

OTHER PUBLICATIONS

Karp et al., "Performance of a Brain PET Camera Based on Anger-Logic Gadolinium Oxyorthosilicate Detectors", Journal of Nuclear Medicine, vol. 44 No. 8, (Aug. 2003), pp. 1340-1349, USA.

* cited by examiner

*Primary Examiner* — David Porta
*Assistant Examiner* — Marcus Taningco
(74) *Attorney, Agent, or Firm* — Harness, Dickey & Pierce, P.L.C.

(57) ABSTRACT

A device for detecting signals is disclosed. In at least one embodiment, the device includes at least four detector elements for receiving the signals and converting them into useful signals, each being connected via at least two lines to at least one signal processing unit. Each detector element includes a polarity reversal unit by which polarity reversal of the useful signal of the respective detector element can be performed. The signal polarity reversal logic is unambiguously spatially direction-dependent within the detector array. An advantage of the device of at least one embodiment is that for signals to be received simultaneously by way of two detector elements, the detector elements involved become unambiguously identifiable by the polarity reversal of the useful signal.

20 Claims, 5 Drawing Sheets

DEVICE FOR DETECTING SIGNALS

PRIORITY STATEMENT

The present application hereby claims priority under 35 U.S.C. §119 on German patent application number DE 10 2008 021 170.2 filed Apr. 28, 2008, the entire contents of which is hereby incorporated herein by reference.

FIELD

At least one embodiment of the present invention generally relates to a device for detecting signals. In at least one embodiment, it relates to a device for detecting signals having at least four detector elements for receiving the signals and converting them into useful signals, the detector elements each being connected via at least two lines to at least one signal processing unit.

BACKGROUND

In addition to magnetic resonance tomography (MR), positron emission tomography (PET) is also being increasingly used in medical diagnostics. While MR is an imaging method for showing structures and slices inside the body, PET allows in vivo visualization and quantification of metabolic activities.

PET uses the particular properties of positron emitters and positron annihilation in order to quantitatively determine the function of organs or cell areas. With this technique, the patient is administered appropriate radiopharmaceuticals marked with radionuclides prior to the examination. As they decay, the radionuclides emit positrons which after a short distance interact with an electron, causing what is termed annihilation to occur. This results in two gamma quanta which fly apart in opposite directions (offset by 180°). The gamma quanta are detected by two opposed PET detector modules within a particular time window (coincidence measurement), by means of which the annihilation site is localized to a position on the line connecting said two detector modules.

In the case of PET, the detector module must generally cover the greater part of the gantry arc length for the purpose of detection. It is subdivided into detector elements having a side length of a few millimeters. On detecting a gamma quantum, each detector element generates an event record that specifies the time and the detection location, i.e. the corresponding detector element. These items of information are transmitted to a fast logic unit and compared. If two events coincide within a maximum time period, it is assumed that there is a gamma decay process on the connecting line between the two associated detector elements. The PET image is reconstructed using a tomography algorithm, i.e. so called back projection.

For PET examinations, measurement data is typically obtained by several hundred detector elements in a precisely timed manner. Only events which are detected simultaneously within a time window by two sensors are actually evaluated. In PET scanners, the signals are digitized and mathematically evaluated close to the detector elements.

In combined MR/PET scanners, the PET gantry must be incorporated close to the patient port of the MR/PET equipment, thereby further exacerbating the space problems to be solved anyway with MR scanners. It is therefore desirable to incorporate as few PET unit components as possible in the PET gantry.

Moreover, because of the high static magnetic field required for MR examinations, an evaluating computer must be a certain minimum distance away. In addition, one or more signal processing units, for example, may be disposed outside the PET gantry and even outside the actual MR/PET device. The signals of the detector elements must then be fed out to the signal processing unit(s) via signal lines. Consequently, a plurality of connecting lines to an evaluating signal processing unit are required for evaluating and detecting the signals of the detector elements. This must be implemented in as space-saving a manner as possible, i.e. using as few signal lines as possible.

It is basically possible for digitized components to be incorporated close to the detection unit in the MR tester, for which e.g. fiberoptic transmission of the signals to the evaluating computer is possible. However, interference with the MR system by the RF components required for this purpose cannot be eliminated, resulting in image artifacts in the MR system.

Crystals which can detect several events are frequently used as detector elements. These are structured, for example, as a 3×3 matrix. Here nine detection units are therefore combined to form one detector element. With an arrangement of this kind it is possible for the nine detection units to be read out using a reduced number of signal lines. This reduction in the signal lines is possible through suitable analog calculating of the signals of the detection units. So-called Anger logic is frequently used for the calculation, in which the barycentric coordinates (X, Y) of the scintillation in the detector and its summed energy are determined in an analog manner and transmitted. Only 3 signal lines (and ground connection) are therefore required for the 3×3 matrix (or other detector arrangement). This has been disclosed by Karp et al. in "Performance of a Brain PET Camera Based on Anger-Logic Gadolinium Oxyorthosilicate Detectors", Journal of Nuclear Medicine, Vol. 44 No. 8, (2003), 1340-1349, the entire contents of which is hereby incorporated herein by reference.

In RF technology it is already known to connect a plurality of signal sources to a plurality of amplifier elements via a switching matrix. The switching matrix used comprises a number of intersecting transmission lines which can be multiply used by switching elements at their points of intersection, said number corresponding to the number of signal sources and amplifier elements. The matrix-like structure enables each signal source to be connected to each amplifier element. This enables the number of signal lines to be significantly reduced compared to implementing the connection between the components by means of individual signal lines. An arrangement of this kind is disclosed, for example, in DE 10 2004 055 939 B4, the entire contents of which is hereby incorporated herein by reference.

SUMMARY

In at least one embodiment of the present invention, a device is provided for detecting signals, with the aid of which a large number of useful signals can be transmitted using a substantially reduced number of cables.

According to an embodiment of the invention, a device is specified for detecting signals using at least four detector elements for receiving the signals and converting them into useful signals. The detector elements are each connected to at least one signal processing unit via at least two lines. At least two of the detector elements are jointly connected to the signal processing unit via one of the lines. Compared to known arrangements in which each detector element is connected to the signal processing unit via an individual line, at least one line is saved here. The number of lines saved increases with the number of detector elements. This is advantageous particularly where space is at a premium for implementing the device. It in particular exploits the fact that, in the case of PET measurements, only combinations of two detector elements need to be evaluated. It is not therefore necessary for all the detector elements to be read out simultaneously, i.e. in parallel.

An embodiment of the invention is advantageous in that the detector elements are arranged in terms of circuitry in rows and columns, all the detector elements of a row being connected to the signal processing unit via one of the lines and all the detector elements of a column being connected to the signal processing unit via another of the lines. The expression "in terms of circuitry" should be understood here as meaning that the detector elements are wired as if they were also geometrically arranged in rows and columns. The detector elements are not generally arranged geometrically in rows and columns. Through the row by row and column by column use of lines and their connections to a plurality of detector elements, the respective detector elements are located effectively at the intersections of the lines.

In an advantageous embodiment of the invention, each detector element comprises a polarity reversal unit by means of which the polarity of the useful signal of the respective detector element can be reversed. The particular advantage of this is that, in the case of simultaneous detection of events by two detector elements, by reversing the polarity of the useful signal of one of the detector elements it is possible for the triggering detector elements to be unambiguously identified.

An embodiment of the invention is advantageous in that each of the detector elements has at least one signal output for the useful signal and the polarity reversal units are connected to the signal outputs of the detector elements in such a way that, when a PET event is present at a first of the detector elements, at least one second of the detector elements that is not connected to the signal processing unit via the same line as the first detector element is reversed in polarity.

Simple, automatic polarity reversal of the corresponding detector elements can be achieved by connecting the signal outputs to the polarity reversal units in this way.

In an advantageous embodiment of the invention, the signal outputs of detector elements located in one of the columns are each connected via a blocking unit to a column line in which blocking units are disposed which are implemented such that it is possible for current to flow through them in one direction only. This enables useful signals of the detector elements located in a column to be combined on one line. It is therefore unnecessary for useful signals of each individual detector element to be carried via a separate line. Blocking units are used to prevent crosstalk of a useful signal into non-detecting detector elements.

An embodiment of the invention is advantageous in that the signal outputs of the detector elements located in a row are connected to a row line via a blocking unit in each case, further blocking units being disposed in the row line and the blocking units being implemented such that current can flow through them in one direction only.

In an advantageous embodiment of the invention, each of the detector elements is assigned a reference signal unit in which the signal present on the column line and present on the row line is processed and fed to the polarity reversal unit of the respective detector element such that, when a PET event is detected in a first of the detector elements, a polarity reversal signal is generated in all the polarity reversal units of detector elements which are, in terms of circuitry, to the right thereof and not in the same row. Here the expression "in terms of circuitry" is again intended to establish a relationship to a matrix-like equivalent circuit (rows and columns). To achieve the object of the embodiment of the invention described here, it is not necessary for all the detector elements which are not in the same row and not in the same column as the first detector element to be reversed in polarity. It suffices if the detector elements not in the same row which are to the left or right of the column of the first detector element are reversed in polarity.

In an advantageous embodiment of the invention, the reference signal unit is connected to the column line and the row line and has a signal output connected to the polarity reversal unit of the respectively assigned detector element, at which output a reference signal is provided by the reference signal unit if and only if a signal is present on the column line and no signal is present on the row. The use of the reference signal unit and the circuitry described here comprising the column line and the row line in which blocking units are disposed, precisely implements automatic polarity reversal of the desired detector elements when an event is present on a first of the detector elements. Precisely those detector units are polarity-reversed that are either to the left or right of the first detector element and not in the same row.

An embodiment of the invention is advantageous in that the reference signal unit comprises a negating unit and a logic unit, wherein:

the negating unit has a signal output and is connected to the row line and implemented such that it provides a signal at the signal output when no input signal is fed to it and provides no signal at the signal output when an input signal is fed to it, the logic unit is implemented such that two input signals can be fed to it and it produces a signal at a signal output when two input signals are fed to it, and the logic unit is connected on the input side to the column line and the negating unit.

This configuration of the reference signal unit represents the condition that a reference signal is only provided for the polarity reversal unit of the respective detector element if no row signal, i.e. no PET event, is present in the respective row, and if a PET event is present in one of the preceding columns.

BRIEF DESCRIPTION OF THE DRAWINGS

Further advantages and embodiments of the invention will emerge from the examples described below with reference to the accompanying drawings in which.

DETAILED DESCRIPTION OF THE EXAMPLE EMBODIMENTS

Figure 1:
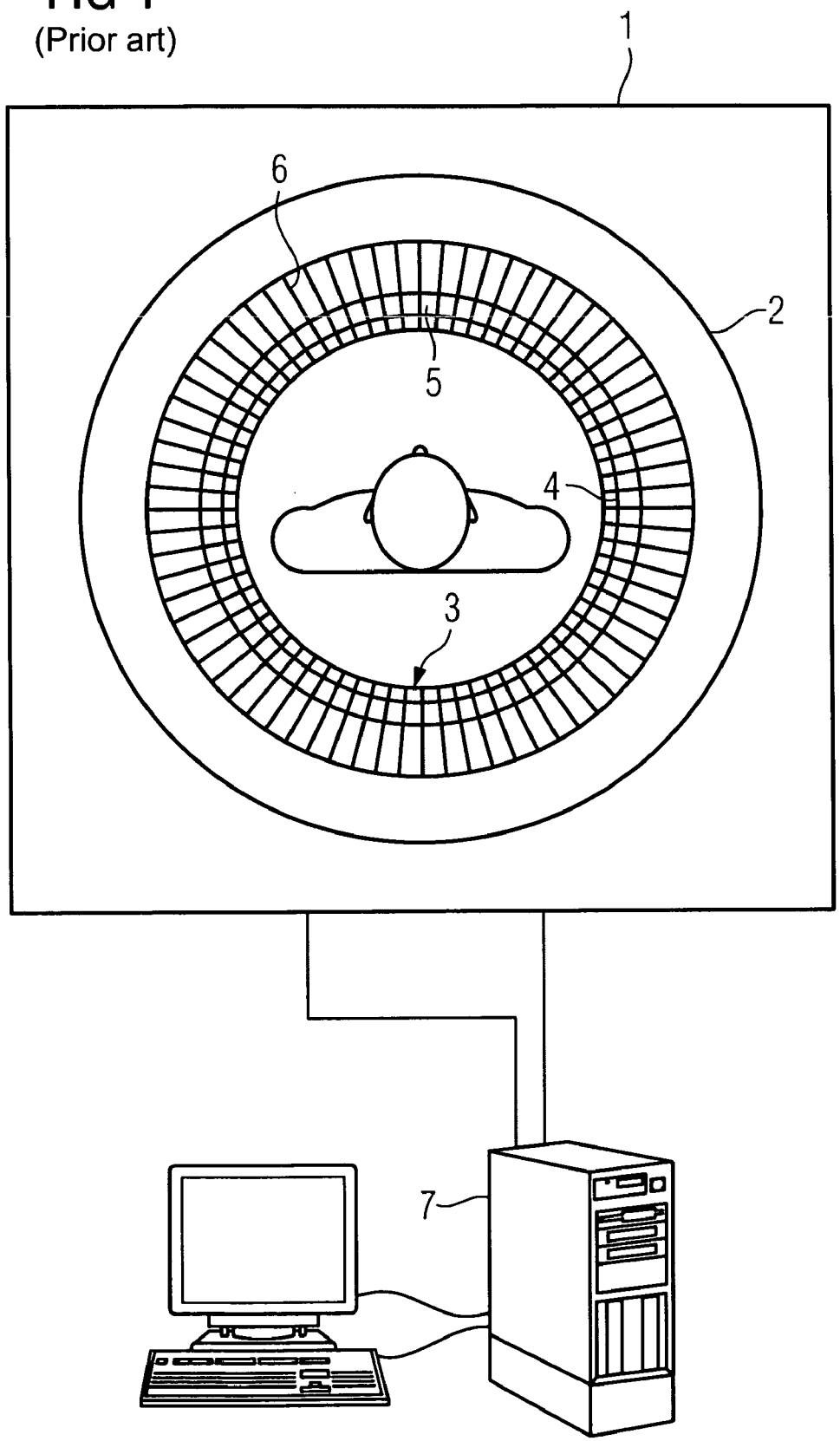
FIG. 1 schematically illustrates a combined MR/PET scanner.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The example embodiments of the invention can be advantageously used in a combined MR/PET scanner. The advantage of a combined device is that both MR and PET data can be isocentrically obtained simultaneously. This enables the examination volume within the region of interest to be precisely defined using the data of the first modality (PET) and this information to be used in the other modality (e.g. magnetic resonance).

Although it is possible to transmit the volume information of the region of interest from an external PET scanner to an MR scanner, this involves increased complexity for registering the data. In general, all the data that can be determined using magnetic resonance or other imaging methods can be ascertained at the region of interest selected on the PET dataset. Instead of the spectroscopy data, for example, fMRI data, diffusion cards, T1 or T2 weighted images or quantitative parameter cards can also be obtained by way of magnetic resonance examinations in the region of interest. Computed tomography (e.g. perfusion measurement, multiple energy imaging) or x-ray methods can likewise be used. The advantage of the method described is that the region of interest can be very selectively narrowed down to a specifically presenting patient pathology by means of the PET dataset.

In addition, however, by using a plurality of so-called tracers, it is also possible to represent different biological properties in the PET dataset, thus optimizing still further the region of interest and the volume determined thereby, or to select a plurality of different examination volumes all at once, which are then analyzed in subsequent examinations.

FIG. 1 shows the known device 1 for overlaid MRI and PET image representation. The device 1 consists of a known MRI tube 2. The MRI tube 2 defines a longitudinal direction z which extends orthogonally to the drawing plane of FIG. 1.

As shown in FIG. 1, a plurality of PET detection units 3 arranged in opposing pairs about the longitudinal direction z are disposed coaxially inside the MRI tube 2. The PET detection units 3 preferably include an APD photodiode array 5 with an upstream array of LSO crystals 4 and an electrical amplifier circuit (AMP) 6. However, the invention is not limited to the PET detection units 3 with the APD photodiode array 5 and the upstream array of LSO crystals 4, as other types of photodiodes, crystals and devices can just as well be used for detection.

The image processing for the overlaid MRI and PET image representation is performed by a computer 7.

Along its longitudinal direction z, the MRI tube 2 defines a cylindrical first field of view. The plurality of PET detection units 3 define, along the longitudinal direction z, a cylindrical second field of view. According to the invention, the second field of view of the PET detection units 3 essentially coincides with the first field of view of the MRI tube 2. This is implemented by appropriately adapting the disposition density of the PET detection units 3 along the longitudinal direction z.

Figure 2:
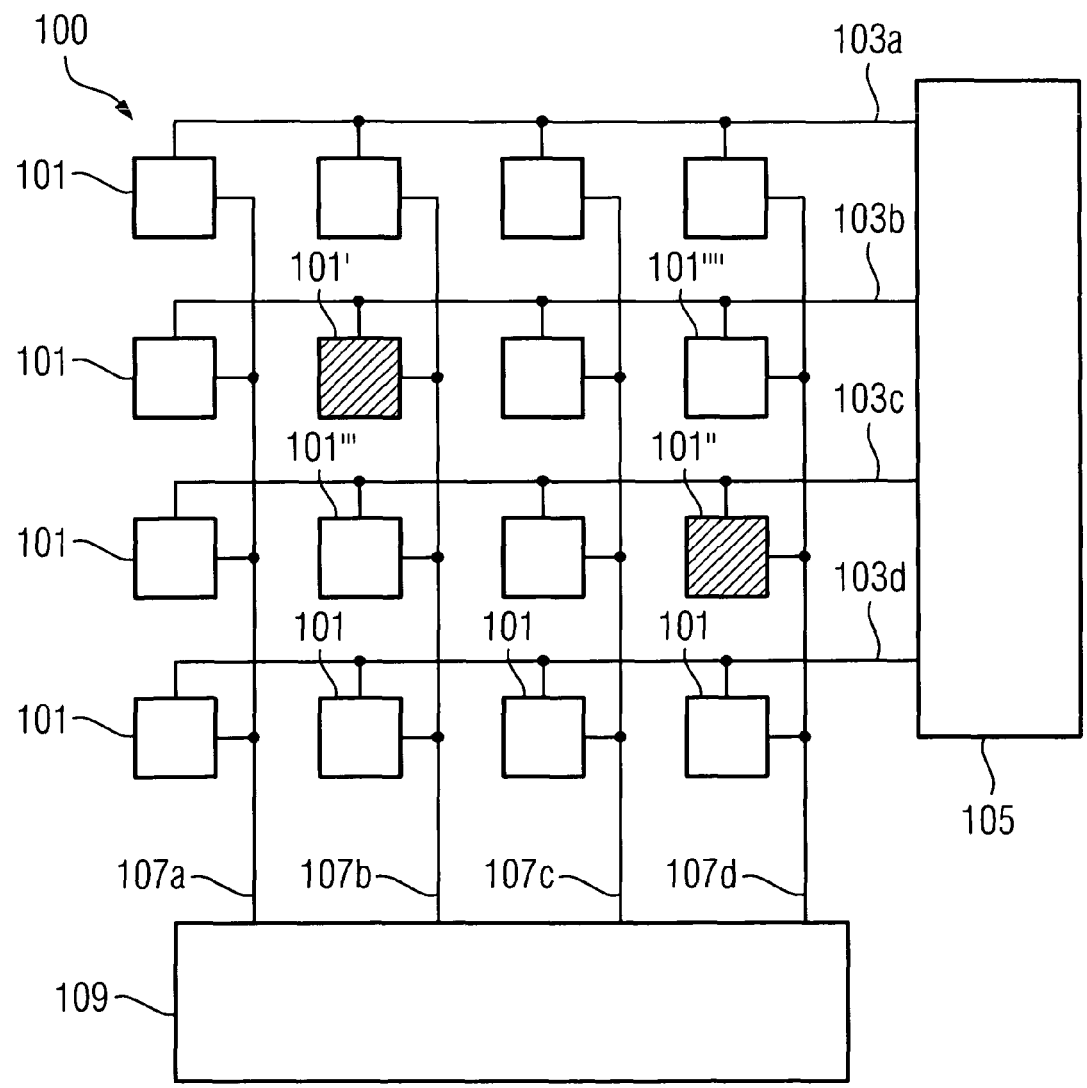
FIG. 2 shows a PET array according to an embodiment of the invention.

FIG. 2 schematically illustrates a detector array as a crossbar switch 100. It includes detector elements 101 arranged in rows and columns. The detector elements 101 arranged in rows are connected to a signal processing unit 105 via lines 103*a*, 103*b*, 103*c*, and 103*d*. The detector elements 101 arranged in columns are connected to a signal processing unit 109 via lines 107*a*, 107*b*, 107*c* and 107*d*. Consequently, each of the detector elements 101 is connected both to the signal processing unit 105 and to the signal processing unit 109. By way of such an arrangement and electrical wiring of the detector elements 101 it is achieved that only eight lines 103*a* to 103*d* and 107*a* to 107*d* are required in order to enable all the detector elements 101 to be read out. Sixteen lines would be required for individual readout and control of the detector elements 101 because of their number.

Alternatively, the signal processing units 105 and 109 can also be implemented as a single common signal processing unit. In this case each of the detector elements 101 would be connected to the signal processing unit via the corresponding lines 103*a* to 103*d* and 107*a* to 107*d*. Likewise, instead of the two signal processing units 105 and 109, a plurality of signal processing units could be provided. The wiring of the detector elements 101 with the signal processing units would have to be selected accordingly.

In the present example embodiment, the detector elements 101 are implemented as PET detectors. In this case only coinciding events of two detector elements 101 are of interest in the signal processing. It is therefore necessary to be able to unambiguously identify such events. It is basically possible to apply embodiments of the invention to other example embodiments using any detector elements.

By way of example, two of the detector elements 101' and 101" are shown cross-hatched in FIG. 2. These are meant to have simultaneously detected two gamma quanta of a PET relevant process. "Simultaneously" shall in this case also include a time difference between two events that is usual in PET processes. The detection of the two gamma quanta by the detector elements 101' and 101" would therefore be a relevant event for a PET measurement. The detector element 101' is connected via the lines 103*b* and 107*b* to the signal processing units 105 and 109 respectively. Corresponding signal levels are transmitted from the detector element 101' to the signal processing units 105 and 109 via the lines 103*b* and 107*b*. The same applies to the detector element 101" and the lines 103*c* and 107*d*. The useful signals of the detector elements 101' and 101" are received and processed in the signal processing units 105 and 109 respectively.

However, by way of the selected arrangement and wiring of the individual detector elements 101 it is not possible, without further measures, for the signal processing units 105 and 109 to unambiguously identify the triggering detector elements 101' and 101". Due to the fact that useful signals are present only on the two lines 103*b* and 103*b* and 107*b* and 107*d* respectively, it would likewise be quite possible for the events to have taken place in the detector elements 101'''' and 101'''' which are likewise connected to the signal processing units in 105 and 109 via the same lines 103*b* and 103*b* and 107*b* and 107*d* respectively. In this case, instead of the associated lines 103*b* and 107*b* and 103*c* and 107*d*, the lines 103*b* and 107*d* and 103*c* and 107*b* would together forward a signal of the detector element 101'''' and 101''' to the signal processing unit 105 and 109 respectively. Unambiguous identification of the associated lines by means of the signal processing units 105 and 109 is not possible.

However, to evaluate the PET examination data it is imperative to be able to unambiguously identify the position of the detector elements 101' and 101". As will be shown in the following, it is therefore possible in the present example embodiment for the polarity of the signal level forwarded from the detector element 101" via the lines 103*c* and 107*d* to the signal processing units 105 and 109 to be reversed compared to the signal level of the detector element 101'. This means that, in the present case, a negative signal level is present on the lines 103*c* and 107*d*, whereas a positive signal level is present on the lines 103*b* and 107*b*. As the signal levels are always of identical polarity on one and the same detector element 101, ambiguity is respect of the detector elements 101''' and 101'''' is no longer possible. The detector elements 101' and 101" are therefore unambiguously identifiable as the detector elements at which PET process events have taken place.

In the cases in which the two detector elements 101 at which an event is present are in the same row or in the same column of the crossbar switch 100, any mistaking of the detector element pair is ruled out anyway. This is due to the fact that, for example, in the first case a signal is only present on one of the lines 103*a* to 103*d*, but on two of the lines 107*a* to 107*d*. Polarity reversal of the detector elements 101, as described above, is therefore not required, but possible, without influencing the measurement result.

A simple possibility for implementing the polarity reversal logic is to provide a corresponding polarity reversal unit in the detector elements 101. This would perform inversion, i.e. polarity reversal of the signal of the detector element 101, when a corresponding control signal is applied. For this purpose, the polarity reversal unit could be connected using a cable on which a corresponding control signal is present. The control signal could be generated, for example, by the signal processing units 105 and 109 and the polarity reversal of the detector elements 101 controlled accordingly.

To achieve this, it would be necessary, for example, to reverse the polarity of all the detector elements 101 that are to the right of the detector element 101' and not in the same row as the detector element 101' in the matrix arrangement in FIG. 2. The detector element 101' is here representative of the detector element 101 which receives a signal and is at the same time disposed farthest left in the matrix.

Conventionally, however, it is likewise possible to use the detector element 101" and to reverse the polarity of all the detector elements to the left thereof which are not in the same row.

An alternative option for implementing the polarity reversal logic is to wire the detector elements 101 together such that, when an event occurs at the detector element 101', the corresponding detector elements 101 are automatically reversed in polarity.

Figure 3:
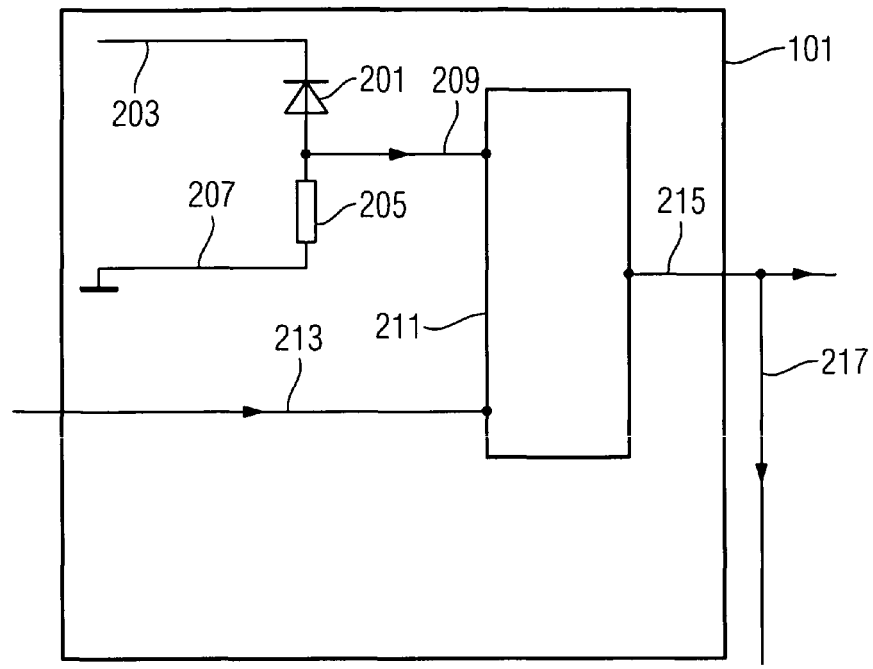
FIG. 3 shows a PET detector element.

FIG. 3 schematically illustrates a detector element 101. It comprises a detection unit 201 which is implemented as a scintillation counter. For its operation, the detection unit 201 is supplied with voltage via a line 203. The corresponding voltage supply is not shown here. The detection unit 201 is grounded via a resistor 205 and a line 207. The detection unit 201 is connected to a polarity reversal unit 211 via a line 209. The polarity reversal unit 211 is connected to a reference line 213. Via said reference line 213, the polarity reversal unit 211 can be fed a reference signal which controls the polarity reversal state of the polarity reversal unit 211. The polarity reversal unit 211 is provided with a line 215 via which the detector signal can be fed out from the detector element 101. To establish the matrix structure, the line 215 is connected to a line 217. The detector element 101 is connected to the signal processing units 105 and 109 via the lines 215 and 217 respectively.

When gamma radiation is incident, the detection unit 201 generates on the line 209 a voltage which fed into the polarity reversal unit 211. In the polarity reversal unit 211, the voltage generated by the detection unit 201 is reversed in polarity if a reference signal is present on the reference line 213. The voltage reversed in polarity in this way is fed out onto the line 215. If no reference signal is present on the reference line 213, the voltage generated by the detection unit 201 is transmitted unchanged to the line 215.

The subsequent figures show interconnections of the detector elements 101 whereby, if PET events are present, an appropriate reference signal is generated which then ensures polarity reversal of the required detector elements 101 via the reference line 213. For this purpose, the matrix-like structure of the detector elements 101 already shown in FIG. 2 is used, this serving merely to provide a simplified illustration. In an actual implementation of the exemplary embodiment and the invention on which it is based, the detector elements 101 are e.g. annularly disposed in an MR system, the additional electronics being disposed in as space-saving a manner as possible in the MR system. For reasons of clarity, the lines 103 to 103d and 107a to 107d already shown in FIG. 2 are not shown in the subsequent schematic drawings.

Figure 4:
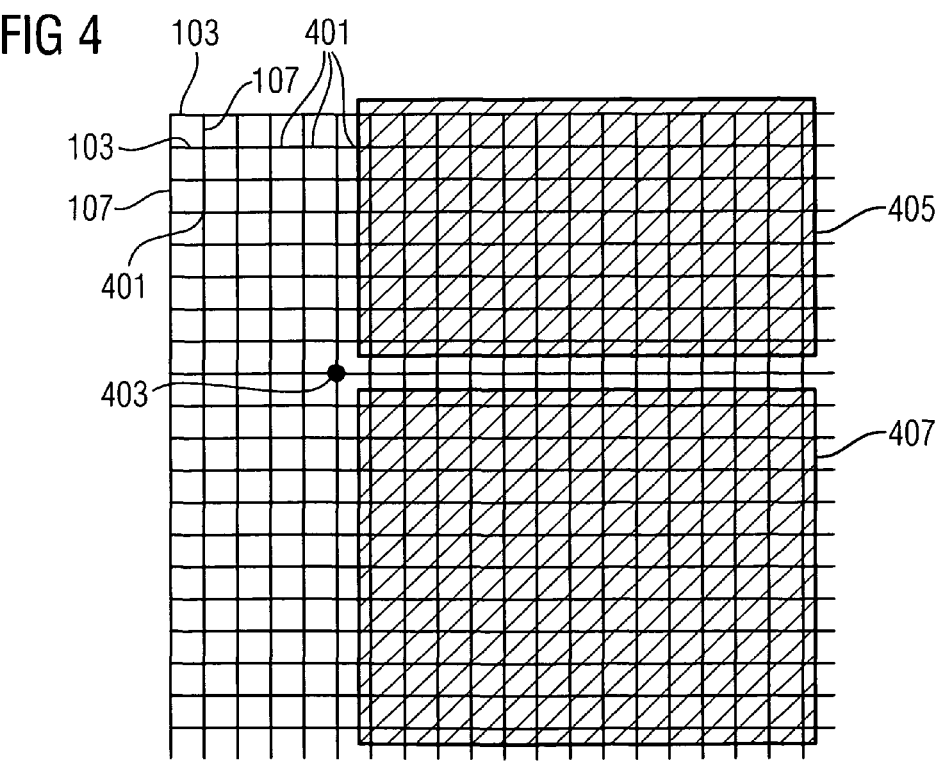
FIG. 4 shows an overview of a PET array.

FIG. 4 schematically illustrates the lines 103' and 107' of a crossbar switch. The lines 103 and 107 are intersecting, a detector element (nor shown here) being disposed at each intersection 401 and connected to the lines 103 and 107. A PET event has been registered at one of the detector elements, which is represented by a point 403. According to the polarity reversal logic described above, all the detector elements to the right of the point 403 that are not in the same row as the point 403 must now be reversed in polarity in accordance with the convention selected. The affected detector elements are indicated by cross-hatched areas 405 and 407 in FIG. 4. The polarity reversal shown ensures, in the relevant cases, that another detector element at which a coinciding event is present lies within the polarity-reversed area. As already explained, unambiguous identification of detector element pairs is possible.

However, the case is also possible that the second detector at which the coinciding event is detected is in the same row or in the same column as the first detector element. Here signals would be transmitted to the signal processing units via the same line of the affected row and via two lines of the affected columns and via the same line of the affected columns and via two lines of the affected rows respectively. In these cases, ambiguity is eliminated at the outset, so that polarity reversal of the second detector element is not required. However, the above described automatic polarity reversal of the detector elements of the cross-hatched areas 405 and 407 is possible in this case without affecting the signal to be detected.

It is desirable that, when a PET event is present at the detector element of the point 403, polarity reversal of the detector elements inside the cross-hatched areas 405 and 407 takes place automatically by appropriate interconnection of the detector elements. For this purpose it is possible to use the output signal of the detector element at the point 403 in order to provide, at the required detector elements of the areas 405 and 407, a corresponding reference signal for the polarity reversal unit 211 shown in FIG. 2. However, it is not possible to simply transmit the output signal in all the detector elements to the right of the point 403, as in that case the detector elements in the row of the point 403 would also be reversed in polarity. This would then again result in ambiguity in the signal processing units 105 and 109. It must therefore be ensured that no polarity reversal takes place in the detector elements of the row of the point 403. It being stipulated that the point 403 is in row i and column j, all detector elements for which the two conditions "column>j" and "row≠i" are simultaneously fulfilled must consequently be reversed in polarity.

The first condition "column>j" can be constituted, for example, by the signal outputs of the detector elements of the column j being connected in parallel, thereby ensuring that, if a PET event is present in a detector element of the column j, a positive reference signal is provided for the polarity reversal unit 211. The second condition "row≠i" can be represented by the digital outputs of the detector elements of the row i being connected. Prior to an ANDing of the column signal and the row signal, the row signal must be inverted. The resulting reference signal can then be fed to the respective polarity reversal unit 211. A possible implementation of such an interconnection of the detector elements will be explained with reference to FIGS. 5 to 8.

Figure 5:
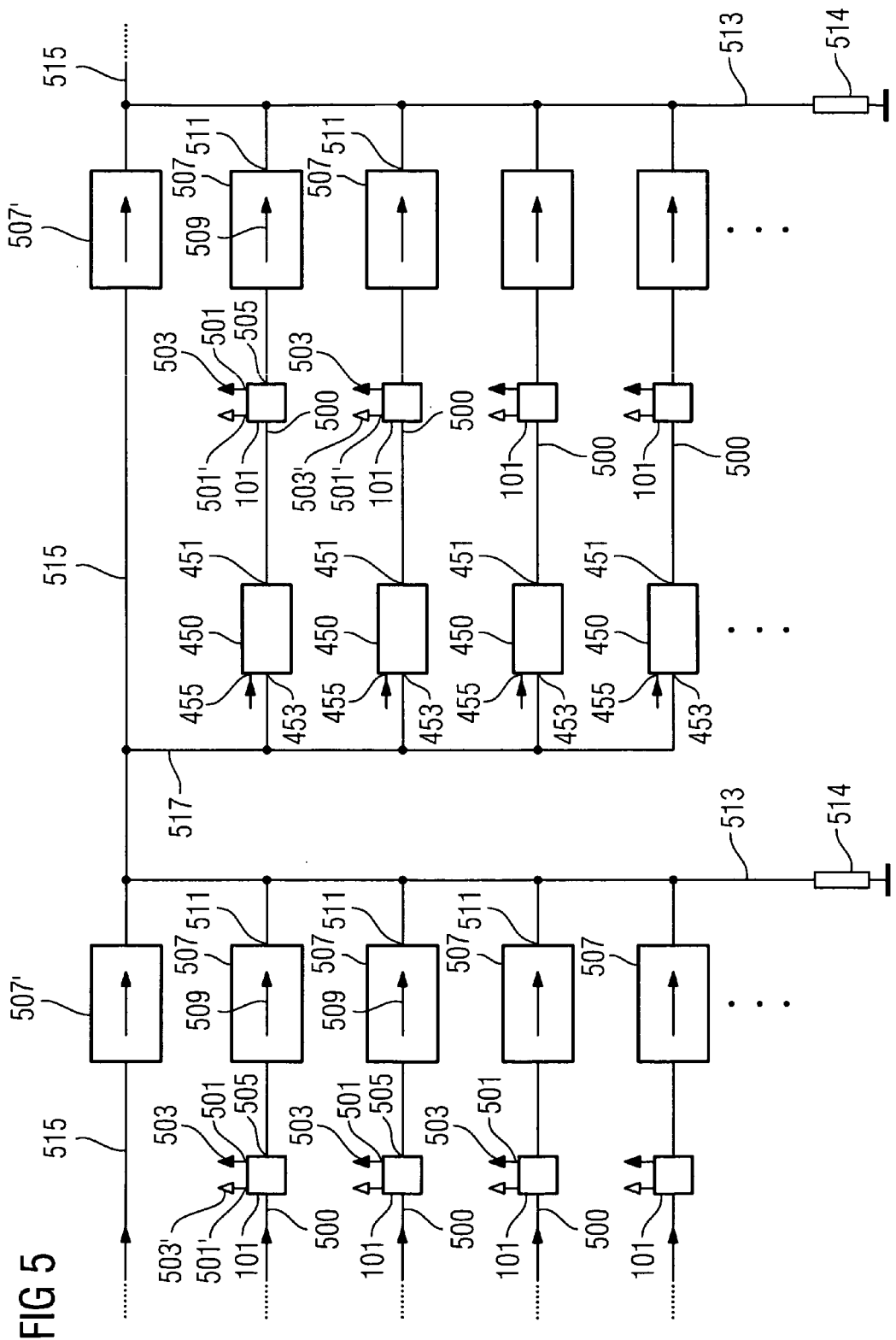
FIG. 5 shows a circuit for generating a column signal.
Figure 6:
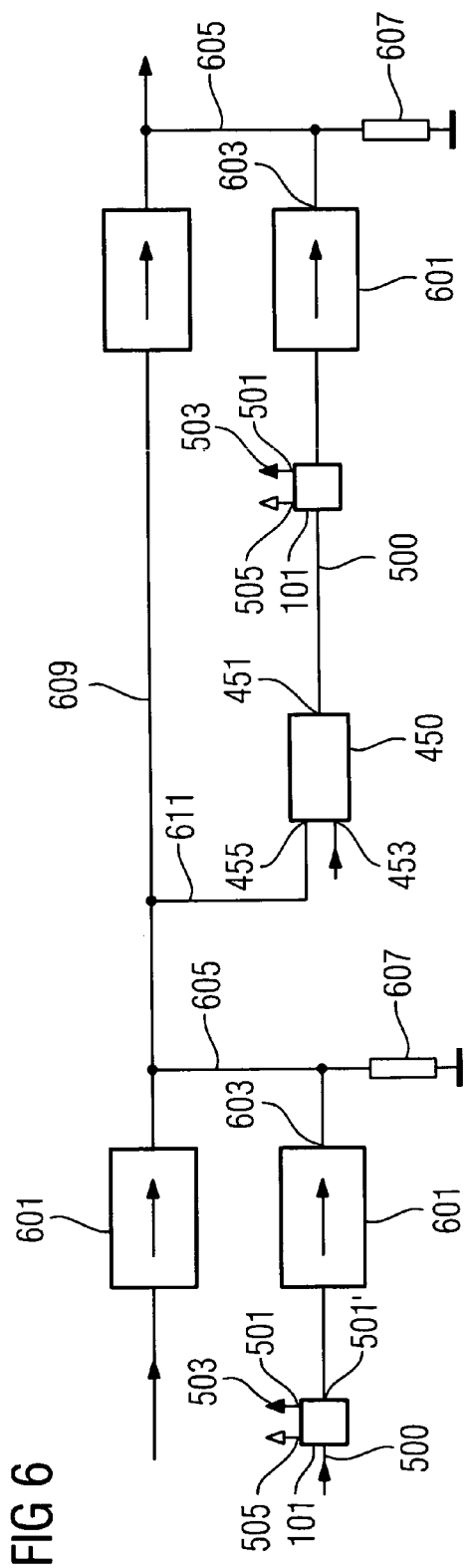
FIG. 6 shows a circuit for generating a row signal.
Figure 7:
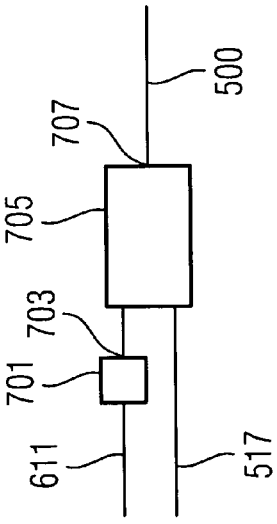
FIG. 7 shows a circuit for generating a reference signal.

FIG. 5 schematically 8 illustrates detector elements 101. They are arranged in two columns and four rows. This arrangement only represents part of an actual detector array which normally comprises many more detector elements 101. Each detector element 101 has an input for a polarity reversal line 500 by which a reference signal can be fed to the respective polarity reversal unit 211 within the detector elements 101. For generating the reference signal, each detector element 101 is assigned a reference signal unit 450. For reasons of clarity, only the reference signal units 450 of the detector elements 101 disposed in the right-hand column are shown in FIG. 5. Each reference signal unit 450 has a signal output 451 which is connected to the polarity reversal line 500 and therefore to the respective polarity reversal unit 201. The reference signal unit 450 also has two signal inputs 453 and 455 via which two signals are fed to generate the reference signal. The generation and feeding of these two signals are shown in FIGS. 5 and 6. The generation of the reference signal is shown in FIG. 7.

The diagram in FIG. 5 only shows the wiring of the detector elements 101 for creating the first condition "column>j". The actual signal lines (cf. FIG. 2) for forwarding the signals of the detector elements to the corresponding signal processing units are not shown here. Each detector element 101 comprises two signal outputs 501 and 501' via which, when a PET event is present, the output signal of the detector is, on the one hand, transmitted to the crossbar switch and, on the other, used for creating the second condition. The latter is shown in FIG. 6. The tapping of the output signals is indicated by an arrow 503 or 503'.

The same output signal of the detector element 101 is provided in each case via another signal output 505 and transmitted to a blocking unit 507. The blocking unit 507 is implemented such that current can only flow in the direction of the arrow 509. Current flow in the opposite direction is suppressed. A design of the blocking unit 507 is shown schematically in FIG. 8. The blocking unit 507 can contain, for example, an amplifier element by which the input signal level is amplified. A correspondingly amplified signal level is provided at an output 511 of the blocking unit 507. The outputs 511 of the blocking units 507 are connected column-wise to a line 513 and thereby connected in parallel. The blocking units 507 prevent current from flowing to the detector elements 101 when a signal is present on the line 513. The line 513 is grounded at one end via a high-value resistor 514. The other end of the line 513 is connected to a column line 515. Said column line 515 interconnects the respective lines 513 of the individual columns, a blocking unit 507' being inserted in each case.

Therefore, as soon as one of the detector elements registers a PET event, the corresponding output signal is transmitted via the assigned blocking unit 511 onto the line 513 and correspondingly onto the column line 515 (column signal). Due to the combining of the column line 515 with all the other columns and the insertion of the blocking units 507' in the column line 515, the output signal is only transmitted to all the columns to the right of the column containing the signal-emitting detector element 101. The blocking element 507', on the other hand, blocks transmission of the column signal to all the columns farther to the left.

To control the polarity reversal units 211 in the detector elements 101, the column signal is branched off from the line 515 by means of a line 517 and transmitted to the signal input 453 of the reference signal unit 450. An interconnection of the detector elements for forming the second signal for the reference signal unit 450, which is fed via the signal input 455, is shown in FIG. 6. The formation of the reference signal for controlling the polarity reversal units 211 is shown in FIG. 7. There the output signal forwarded on the line 517 undergoes further processing.

FIG. 6 shows a wiring arrangement of the detector elements 101 by which the output signal is partially tapped off. The reference signal for controlling the polarity reversal units 211 is generated by further processing by way of the circuit shown in FIG. 7.

FIG. 6 shows part of a PET array with two detector elements 101 in a row. As in FIG. 5, they each have a polarity reversal line 500 by which the reference signal can be fed into the detector element 101. As in FIG. 5, the detector elements 101 have three signal outputs 501, 501' and 505. Analogously to the illustration in FIG. 5, the output signal can be fed into the crossbar switch via the signal output 501 (cf. FIG. 2). This is indicated by the arrow 503. The output signal can be transmitted to the respective blocking unit 507, as shown in FIG. 5, via the signal output 505 shown here on the upper part of the detector element 101. The circuits in FIGS. 5 and 6 are to this extent independent of one another in respect of the signal outputs.

The output signal of the respective detector element 101 can be transmitted via the signal output 501' to blocking units 601 which are comparable to the blocking units 507. The blocking units 601 for their part have outputs 603 at which a correspondingly processed signal is provided. This is transmitted onto a line 605 which is grounded at one end via a resistor 607. At its other end, the line 605 is connected to a row line 609 onto which the signal is transmitted (row signal). In this way the row line 609 connects all the outputs 603 of the blocking units 601 of a row in parallel, a blocking unit 601 being disposed upstream of the junction with a line 605 in each case. The arrangement of the blocking units 601 in the row line 609 and between the detector element 101 and the line 605 ensures that currents flowing on the row line 609 only flow to the right and are blocked in leftward directions in the selected representation. Current flowing on the row line 609 is at the same time prevented from reaching the detector element 101. To form the reference signal, the row signal flowing on the row line 609 is branched off onto a line 611 and transmitted to the signal input 455 of the reference signal unit 450. Two signals (column signal and row signal) are therefore available in each case at the reference signal units 450 for forming the reference signal. The column signal is generated from the parallel connection of all detector elements 101 of a column and transmitted in parallel to all the reference signal units 450 of the adjacent columns. The row signal, on the other hand, is transmitted in a row-specific manner from a detector unit 101 to all reference signal units 450 in the same row. The circuits shown in FIGS. 5 and 6 are independent of one another. Only the detector elements 101 and the assigned reference signal units 450 are the same units in both figures.

FIG. 7 schematically illustrates a circuit 700 for processing the signals tapped off in the lines 517 and 611. The line 611 is connected to a negating unit 701. Said negating unit 701 provides a signal at its signal output 703 if no row signal is present on the line 611. Conversely, no signal is provided at the signal output 703 if a row signal is applied to the negating unit. Consequently, a signal level according to the second condition "row≠i" is present at the signal output 703 of the negating unit 701.

The output signal of the negating unit 701 is transmitted to a logic operator 705. The column signal is likewise transmitted to the logic operator 705 via the line 517. The logic operator 705 only provides an output signal at its signal output 707 in the cases in which it receives a signal from the negating unit 701 and a column signal via the line 517. This corresponds to a logical ANDing of the two conditions "columns>j" and "row≠i". The signal output 707 of the logic operator 705 is connected to the polarity reversal line 500 so that, in the polarity reversal unit 211 of the detector elements 101, said ANDed conditions are present as a reference signal and control the polarity reversal process accordingly.

Each of the detector elements 101 is assigned a circuit 700 which controls the polarity reversal process of the detector element accordingly. The column signal of the previous column in each case is injected into the line 517. The column signal is consequently identical for all the circuits 700 of a column. The row signal present on the row line 609 of the respective row of detector elements 101 is injected into the line 611 in each case. This signal is consequently different for each row. Through the linking of the emitted row signal and the column signal, a scintillation event of a detector element 101 affects all the detector elements 101 to the right of the detector element 101 that are not in the same row. That is to say, in the same row the row signal is finite so that no signal is present at the output 703 of the negating unit 701. Then, however, no signal is present either at the signal output 707 of the logic operator 705, and the detector elements in the same row are not reversed in polarity. This only takes place when a finite signal level is present at the signal output 707 of the logic operator 705.

For all the detector elements 101 to the right of and outside the row of the responding detector element 101, a signal is present at the output 703 of the negating unit 701. As in this case the column signal on line 517 is also finite, a reference signal by which the polarity reversal unit 211 is activated in each case is present at the signal output 707 of the logic operator 705. The corresponding detector elements 101 are consequently reversed in polarity.

Figure 8:
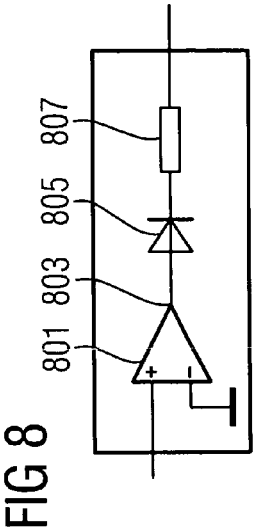
FIG. 8 shows a blocking unit.

FIG. 8 schematically illustrates the design of the blocking units 507 and 601. They each comprise an operational amplifier 801 for amplifying an input signal. The operational amplifier 801 amplifies the input signal as compared to ground and furnishes it at an output 803. The output 803 is connected to a diode 805 which permits current flow in one direction only. In the selected illustration in FIG. 8, this is the left-to-right direction. The output of the diode 805 is connected to a resistor 807. Downstream of the resistor 807, the amplified input signal is provided as an output signal at the output of the blocking unit 507/601. The resistor 807 used can have a value of 1 kΩ, for example. The resistors 515 and 607 for the grounding of the lines 513 and 605 will in this case be selected much larger, e.g. with a value of 1 MΩ.

The dimensioning of the operational amplifier 801, the diodes 805 and the resistors 515, 607 and 807 in the circuits shown in FIGS. 4 to 8 must be adapted to suit the implementations of the respective PET array.

For the example embodiments shown it is irrelevant whether the polarity reversal unit 211 is implemented within the detector element 101 or disposed separately from same. In addition, a single signal output of the detector element 101 can also be used to provide the corresponding signal to the signal lines 103a-d and 107a-d, and to create the two conditions according to the circuits in FIGS. 5 and 6. Likewise, instead of the single detection units 201 (cf. FIG. 2), the detector blocks with a plurality of detection units 201 mentioned in the introduction can be used for each detector element 101. Here the polarity reversal of the polarity reversal unit only affects the actual useful signal of the detector block, whereas the signals which characterize the responding detection unit of the detector block are not reversed in polarity, it being advantageous if the polarity-reversed signal itself has, for physical reasons, a known (e.g. positive) sign such as e.g. typical for a signal proportional to a measured energy. However, this is not imperative. In the case of using the combined detector units with pre-calculated signals (e.g. Anger encoding), polarity reversal of a single signal (e.g. of the energy) is sufficient for unambiguous identification of the two simultaneously active detector elements. To this extent the above explanation can also be applied to the use of combined detector blocks.

In an alternative embodiment of the present invention, it is possible for the polarity reversal units to be controlled not on the basis of an available signal of an event of a detector element, but for separate control lines to be provided. These could run, for example, from the signal processing units 105 and/or 109 shown in FIG. 2 to the polarity reversal units 211 of the detector elements 101. On detection of a PET event at a detector element 101, the signal processing units 105 and/or 109 would each transmit a reference signal to the corresponding polarity reversal units 211 of the desired detector elements 101.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A device for detecting signals, comprising:
at least four detector elements for receiving the signals and converting them into useful signals, each of the at least four detector elements being connected via at least two lines to at least one signal processing unit, at least two of the detector elements being jointly connected to the signal processing unit via one of the lines, wherein the detector elements are disposed in terms of circuitry in rows and columns, all the detector elements of one of the rows being connected to the signal processing unit via one of the lines and all the detector elements of one of the columns being connected to the signal processing unit via another of the lines; and
a device adapted to reverse polarity of the useful signals, implemented to enable pairwise occurring detection events to be unambiguously assigned to a respective one of the at least four detector elements.

2. A device for detecting signals, comprising:
at least four detector elements for receiving the signals and converting them into useful signals, each of the at least four detector elements being connected via at least two lines to at least one signal processing unit, at least two of the detector elements being jointly connected to the signal processing unit via one of the lines; and a means for reversing polarity of the useful signals, implemented to enable pairwise occurring detection events to be unambiguously assigned to the respective detector element.

3. The device as claimed in claim 2, wherein each of the detector elements comprises a polarity reversal unit by which polarity reversal of the useful signal of the respective detector element occurs.

4. The device as claimed in claim 3, wherein each of the detector elements includes at least one signal output for the useful signal and wherein the polarity reversal units are connected to the signal outputs of the detector elements such that, when a PET event is present on a first of the detector elements, at least one second of the detector elements that is not connected to the signal processing unit via the same line as the first detector element is reversed in polarity.

5. The device as claimed in claim 4, wherein the signal outputs of detector elements in one of the columns are connected in each case via a blocking unit to a column line in which blocking units are disposed, the blocking units being implemented such that current can flow through them in one direction only.

6. The device as claimed in claim 5, wherein the signal outputs of the detector elements in a row are connected in each case via a blocking unit to a row line, further blocking units being disposed in the row line and the blocking units being implemented such that current can flow through them in one direction only.

7. The device as claimed in claim 6, wherein each of the detector elements is assigned a reference signal unit in which the signal present on the column line and present on the row line is processed and fed into the polarity reversal unit of the respective detector element such that, when a PET event is detected in one of the detector elements, a polarity reversal signal is generated in all polarity reversal units by detector elements which are, in terms of circuitry, to the right thereof and not in the same row.

8. The device as claimed in claim 7, wherein the reference signal unit is connected to the column line and the row line and has a signal output connected to the polarity reversal unit of the respectively assigned detector element, at which output a reference signal is provided by the reference signal unit if, and only if, a signal is present on the column line and no signal is present on the row line.

9. The device as claimed in claim 8, wherein the reference signal unit comprises:
a negating unit; and
a logic unit, the negating unit being connected to the row line and being implemented to provide a signal at a signal output if no input signal is fed to the negating unit and to provide no signal at the signal output if an input signal is fed to the negating unit, two input signals being feedible to the logic unit, the logic unit providing a signal at the signal output if two input signals are fed to the logic unit and being connected on the input side to the column line and the negating unit.

10. The device as claimed in claim 9, wherein the polarity reversal units are connected to a control unit for controlling the polarity reversal state, the control unit being connected to the signal processing unit and implemented such that polarity reversal of the detector elements takes place as a function of the received useful signals.

11. The device as claimed in claim 10, wherein the control unit is implemented such that, when a useful signal is received from one of the detector elements, the polarity reversal units of those detector elements that are not in the same column and not in the same row as the one detector element are controlled.

12. A device for detecting signals, comprising:
at least four detector elements for receiving the signals and converting them into useful signals, each of the at least four detector elements being connected via at least two lines to at least one signal processing unit, at least two of the detector elements being jointly connected to the signal processing unit via one of the lines; and
a polarity reversal unit, included for each of the detector elements, to reverse polarity of the useful signals.

13. The device as claimed in claim 12, wherein each of the detector elements includes at least one signal output for the useful signal and wherein the polarity reversal units are connected to the signal outputs of the detector elements such that, when a PET event is present on a first of the detector elements, at least one second of the detector elements that is not connected to the signal processing unit via the same line as the first detector element is reversed in polarity.

14. The device as claimed in claim 13, wherein the signal outputs of detector elements in one of the columns are connected in each case via a blocking unit to a column line in which blocking units are disposed, the blocking units being implemented such that current can flow through them in one direction only.

15. The device as claimed in claim 14, wherein the signal outputs of the detector elements in a row are connected in each case via a blocking unit to a row line, further blocking units being disposed in the row line and the blocking units being implemented such that current can flow through them in one direction only.

16. The device as claimed in claim 15, wherein each of the detector elements is assigned a reference signal unit in which the signal present on the column line and present on the row line is processed and fed into the polarity reversal unit of the respective detector element such that, when a PET event is detected in one of the detector elements, a polarity reversal signal is generated in all polarity reversal units by detector elements which are, in terms of circuitry, to the right thereof and not in the same row.

17. The device as claimed in claim 16, wherein the reference signal unit is connected to the column line and the row line and has a signal output connected to the polarity reversal unit of the respectively assigned detector element, at which output a reference signal is provided by the reference signal unit if, and only if, a signal is present on the column line and no signal is present on the row line.

18. The device as claimed in claim 17, wherein the reference signal unit comprises:
a negating unit; and
a logic unit, the negating unit being connected to the row line and being implemented to provide a signal at a signal output if no input signal is fed to the negating unit and to provide no signal at the signal output if an input signal is fed to the negating unit, two input signals being feedible to the logic unit, the logic unit providing a signal at the signal output if two input signals are fed to the logic unit and being connected on the input side to the column line and the negating unit.

19. The device as claimed in claim 18, wherein the polarity reversal units are connected to a control unit for controlling the polarity reversal state, the control unit being connected to the signal processing unit and implemented such that polarity reversal of the detector elements takes place as a function of the received useful signals.

20. The device as claimed in claim 19, wherein the control unit is implemented such that, when a useful signal is received from one of the detector elements, the polarity reversal units of those detector elements that are not in the same column and not in the same row as the one detector element are controlled.

\* \* \* \* \*